US00PP14449P29

(12) United States Plant Patent
Uchneat

(10) Patent No.: US PP14,449 P2
(45) Date of Patent: Jan. 6, 2004

(54) IMPATIENS PLANT NAMED 'BALPIXRED'

(50) Latin Name: *Impatiens walleriana*
Varietal Denomination: Balpixred

(75) Inventor: Michael S. Uchneat, St. Charles, IL (US)

(73) Assignee: Ball Floraplant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/109,410

(22) Filed: Mar. 27, 2002

(51) Int. Cl.[7] ..... A01H 5/00
(52) U.S. Cl. ..... Plt./317
(58) Field of Search ..... Plt./317

*Primary Examiner*—Anne Marie Grunberg
(74) *Attorney, Agent, or Firm*—Wood, Phillips, Katz, Clark & Mortimer

(57) ABSTRACT

A new and distinct Impatiens plant named 'Balpixred', characterized by its small single red flowers, compact growth habit and dark green leaves.

1 Drawing Sheet

Latin name of genus and species of plant claimed: *Impatiens walleriana.*
Variety denomination: 'Balpixred'.

BACKGROUND OF THE INVENTION

The present invention comprises a new and distinct Impatiens plant, botanically known as *Impatiens walleriana* and hereinafter referred to by the cultivar name Balpixred.

'Balpixred' is a product of a planned breeding program with the objective of developing Impatiens cultivars with small flowers and compact growth habits.

The female or seed parent of 'Balpixred', 'Red Chico' (not patented), has a more compact growth habit than 'Balpixred'. The male or pollen parent of 'Balpixred', the proprietary Impatiens selection designated SD01033-2 (not patented), has pink and white bicolor flowers. The new cultivar was discovered and selected as a single flowering plant within the progeny of the above stated cross during January 2000 in a controlled environment at Elburn, Ill. The new cultivar was designated BFP-562.

Asexual reproduction of the new cultivar has been carried out at Elburn, Ill. and West Chicago, Ill. by terminal tip cuttings and has demonstrated that the unique characteristics of the new cultivar as herein described are firmly fixed and retained through successive generations of such asexual propagation.

SUMMARY OF THE INVENTION

It was found that the cultivar of the present invention:

(a) exhibits small red flowers;

(b) forms dark green foliage;

(c) exhibits a good basal branching character; and (d) exhibits a compact growth habit.

The new cultivar of the present invention can be compared to 'Fify Red' (U.S. Plant Pat. No. 11,753). However, in side-by-side comparisons, plants of the new cultivar are more vigorous. Lower surface of leaves of 'Balpixbros' are solid green whereas those of 'Fify Red' are green with blotches of 183D and the flower color of 'Balpixred' is slightly lighter than 'Fify Red'. "Balpixred can also be compared to its sibling cultivar, 'Balpixbros'. In side-by-side comparisons flowers of 'Balpixred' are darker and more red than those of 'Balpixbros'."

BRIEF DESCRIPTION OF PHOTOGRAPH

The accompanying photograph shows as nearly true as it is reasonably possible to make the same in color illustrations of this type, typical flower and foliage characteristics of the new cultivar. The plants were grown for 12 weeks in a greenhouse at West Chicago, Ill.

DETAILED BOTANICAL DESCRIPTION

The cultivar 'Balpixred' has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Feb. 13, 2002. The readings were taken between 2:00 and 3:00 p.m. under natural daylight conditions.

Plants used for the following descriptions and measurements were grown in 10 cm pots for 12 weeks from rooted cuttings. The plants were produced from cuttings taken from stock plants and grown in a double poly carbonate covered greenhouse under conditions comparable to those used in commercial practice. A soilless growth medium was utilized while temperatures of approximately 68° to 75° F. (20° to 24° C.) during the day and approximately 55° to 65° F. (13° to 18° C.) during the night and light levels of 4,000 to 6,000 footcandles were maintained.

Classification:

*Botanical.*—*Impatiens walleriana* cultivar 'Balpixred'.

Parentage:

*Female parent.*—Proprietary Impatiens variety designated 'Red Chico'.

*Male parent.*—Proprietary Impatiens variety designated SD01033-2.

Propagation:

*Type cutting.*—Terminal tip.

*Time to initiate roots.*—Approximately 7 to 10 days.

*Time to develop roots.*—Approximately 21 to 30 days.

*Root description.*—Fibrous, branching.

Plant description:

*Crop time.*—Approximately 4 to 6 weeks are required to produce a finished plant from rooted cuttings.

*Habit of growth.*—Compact with good basal branching. Pinching is not required.

*Form.*—Upright and mounded.

*Height of foliage.*—A mature plant, 12 weeks after the planting of a rooted cutting, commonly measures approximately 17 cm.

*Plant spread.*—Approximately 24.3 cm.

*Lateral branches.*—An average of 16 branches per plant, approximately 8 cm in length and 4 mm in diameter, glabrous and 146C with streaks of 59A. Internode length at the middle of the branch is approximately 4 mm.

*Foliage.*—Arrangement is alternate. Leaves are single, ovate with crenate, ciliate margin, acuminate apex, attenuate base and are at an acute angle to the stem. Upper and lower surfaces are glabrous. Leaf length is approximately 2.9 cm and width is approximately 1.8 cm. The upper surface of mature foliage is 147A and the lower surface is closest to 138B. Both upper and lower surfaces have pinnate venation. Venation of upper surface is 147D and the venation of the lower surface is 147B. The petiole length is approximately 1.9 cm, the diameter is approximately 2 mm and the color is lighter than 147D.

Flowering description:

*Flowering habit.*—Freely flowering.

*Natural flowering season.*—Year round in greenhouse environment and from spring through fall in outdoor garden.

Flower description:

*Type.*—Single and persistent.

*Size.*—Diameter is approximately 1.7 cm.

*Aspect.*—Very slightly cupped.

*Corolla.*—Five petals with entire undulate margin and smooth texture. Upper petal length is approximately 1.1 cm and width at widest point is 1.1 cm. Lower and lateral petal length is approximately 1.4 cm and width is approximately 9 mm. All petals have emarginate apex and attenuate base. Color of upper surface of upper and lateral petals is closest to 46B. Color of lower surface of upper and lateral petals is 44D. Color of upper surface of lower petals is close to 39B with spot of 59C at base. Color of lower surface of lower petals is 44D.

*Peduncle.*—Glabrous, at an acute angle to the stem, approximately 1.7 cm in length and 1 mm in diameter. Peduncle color is 144C.

*Flower bud.*—Oval, approximately 8 mm in length and 5 mm in diameter. Color is 51A.

*Sepals.*—Three. The lateral sepals are lanceolate in shape with acuminate apex and are approximately 2 mm in length and 1 mm in width 144C. The lower sepal is modified into a spur.

*Spur.*—Sharply curved, 2.3 cm in length and 39D.

*Reproductive organs.*—Five stamens, 3 mm in length. Anthers are fused around pistil and 72A. Pollen is sparse and 75A in color. Pistil length is 3 mm. Style length is <1 mm and color is 155D. Stigma length is <1 mm and color is 64A. Ovary is 2 mm in length and 144A in color.

Seed production: Seed production has not been observed.

Disease resistance: Resistance to pathogens has not been observed.

Hardiness zone: 'Balpixred' is hardy in zones nine (9) and above.

I claim:

1. A new and distinct cultivar of Impatiens plant named 'Balpixred' substantially as herein shown and described, which:

(a) exhibits small single red flowers, (b) dark green foliage, (c) a compact growth habit and (d) a good basal branching character.

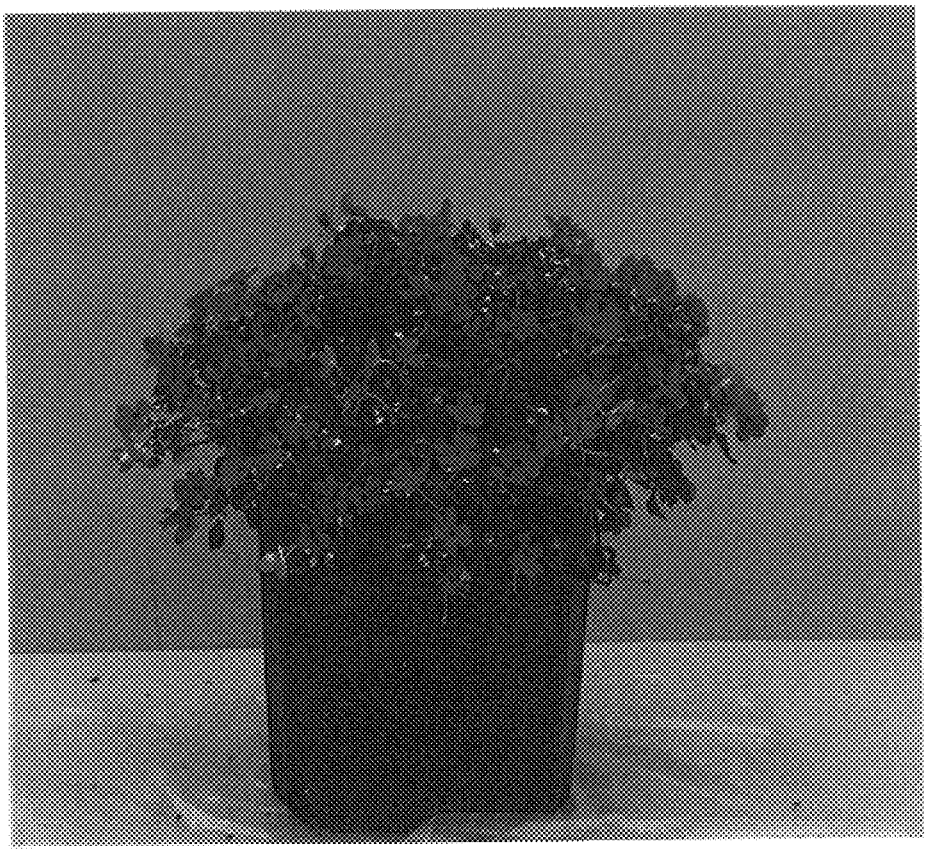

* * * * *